(12) United States Patent
Schaart

(10) Patent No.: US 6,554,756 B1
(45) Date of Patent: Apr. 29, 2003

(54) METHOD FOR MANUFACTURING RADIOACTIVE BRACHYTHERAPY SOURCE MATERIAL, BRACHYTHERAPY SOURCE MATERIAL AND ENCAPSULATED RADIOACTIVE BRACHYTHERAPY SOURCE

(75) Inventor: Dennis Robert Schaart, Ze Delft (NL)

(73) Assignee: Nucletron B.V., Veenedaal (NL)

( * ) Notice: Subject to any disclaimer, the term of this patent is extended or adjusted under 35 U.S.C. 154(b) by 148 days.

(21) Appl. No.: 09/660,637

(22) Filed: Sep. 13, 2000

(30) Foreign Application Priority Data

Sep. 14, 1999 (NL) .............................. 1013036

(51) Int. Cl.[7] .................................. A61N 5/00
(52) U.S. Cl. ........................................... 600/3
(58) Field of Search ................ 600/1–8; 424/1.11, 424/1.29, 1.37; 252/625, 638

(56) References Cited

U.S. PATENT DOCUMENTS

| | | |
|---|---|---|
| 4,510,924 A | 4/1985 | Gray |
| 5,342,383 A | 8/1994 | Good |

FOREIGN PATENT DOCUMENTS

| | | |
|---|---|---|
| WO | WO 97/19706 | 6/1997 |
| WO | WO 99/22812 | 5/1999 |
| WO | WO 00/59550 | 10/2000 |

*Primary Examiner*—Max F. Hindenburg
*Assistant Examiner*—Brian Szmal
(74) *Attorney, Agent, or Firm*—Birch, Stewart, Kolasch & Birch, LLP

(57) ABSTRACT

The invention relates to a method for producing a radioactive brachytherapy source material comprising indium-114m in radioactive equilibrium with indium-114 as main radioactive isotopes. A new radioactive brachytherapy source material comprises indium-114m in radioactive equilibrium with indium-114 as main radioactive isotopes. A new encapsulated radioactive brachytherapy source comprises the new radioactive brachytherapy source material.

7 Claims, No Drawings

METHOD FOR MANUFACTURING RADIOACTIVE BRACHYTHERAPY SOURCE MATERIAL, BRACHYTHERAPY SOURCE MATERIAL AND ENCAPSULATED RADIOACTIVE BRACHYTHERAPY SOURCE

The invention relates to a method for manufacturing radioactive brachytherapy source material.

The invention also relates to a radioactive brachytherapy source material.

The invention also relates to encapsulated radioactive brachytherapy sources comprising a radioactive brachytherapy source material.

BACKGROUND OF THE INVENTION

Brachytherapy as used herein is defined as therapy performed on mammals in which radioactive sources are brought in the near vicinity of tissue to be treated. Conventionally the tissue to be treated was mainly cancerous tissue. Since the early nineteen nineties a new field has started using brachytherapy, namely endovascular brachytherapy of blood vessels that have been subjected to angioplasty. It has been discovered that irradiation of the angioplasty site before, during or after the performance of the angioplasty may significantly reduce restenosis of the site. Restenosis is the re-occlusion of a vessel due to tissue growth and vessel remodeling after the angioplasty procedure. Endovascular brachytherapy has been described in Bertrand, O. F. et al; Intravascular radiation therapy in atherosclerotic disease: promises and premises; European Heart Journal, (1997) 18, pag. 1385–1395; Diamond, D. A. et al; The Role of Radiation Therapy in the Management of Vascular Restenosis. Part II. Radiation Techniques and Results; JVIR (1998)9, pag. 389–400; Baumgart, D. et al; Die intravasale Strahlenbehandlung zur kombinierten Therapie und Prävention der Restenosierung; Herz 1977;22:335–346(Nr.6); Balter, S.; Endovascular Brachytherapy: Physics and Technology; Catheterization and Cardiovascular Diagnosis 45:292–298 (1998) and Nath, R. et al; Intravascular brachytherapy physics: Report of the AAPM Radiation Therapy Committee Task group No. 60; Med. Phys. 26(2), February 1999, pag. 119–152, Ron Waksman (ed): Vascular Brachytherapy, Second Edition, Future Publishing Company, Inc, 1999, Armonk, N.Y. and Waksman, R. et al: Vascular Brachytherapy, Nucletron B. V., 1996, Veenendaal, the Netherlands.

In various applications of brachytherapy a radioactive brachytherapy source is brought into the vicinity of the tissue to be treated through a tube like device such as a catheter. Such a tube like device is also known as a guide tube.

Radioactive brachytherapy sources have been described in a number of patents and other references. An exemplary embodiment of such description is known from U.S. Pat. No. 4,861,520. The source described therein comprises a steel capsule. An opening of the capsule is welded to a plug. The plug is welded in turn to a steel cable. Inside the capsule a number of radioactive iridium-192 pellets is present.

Another exemplary embodiment of a radioactive brachytherapy source may be found in U.S. Pat. No. 5,084,001. Therein is shown and described a relatively pure platinum wire with near one of its tips a rod like piece of iridium-192 fully encapsulated by the platinum.

A further exemplary embodiment of a radioactive brachytherapy source is shown and described in international patent application WO 94/25106. Therein is shown and described a nickel-titanium wire with a longitudinal, axially directed cavity at a tip. That cavity is filled with a number of iridium-192 spheres.

A still further embodiment of a radioactive brachytherapy source is shown and described in international patent application WO 92/00776. Therein is shown and described a source comparable to the source shown in U.S. Pat. No. 4,861,520, however, with a single elongated rod of radioactive material in place of a number of pellets.

Further embodiments of radioactive brachytherapy sources are shown and described in the United States Registry of Radioactive Sealed Sources and Devices. The Registry may be approached through the Internet at website http://www.hsrd.ornl.gov/nrc/ssdr/ssdrindj.htm#J.K Registration No. LA-0557-S-102-S describes and shows an iridium wire encapsulated with a 3 micron titanium coating. The titanium coating forms a hard (flexible) shell around the Ir-192 wire. The Ir-192 wire is positioned and sealed inside a nickel/titanium tube that has a cavity formed by a nickel titanium wire that runs the entire length of the tube and stops short of the last 32 mm. This forms the cavity that accepts the 30 mm long Ir-192 wire. The backbone wire is welded to the distal end of the tube to form a tight seal. The Ir-192 wire is placed into the cavity created inside the tube and the proximal end of the tube is welded shut to firmly encapsulate the Ir-192 wire.

Registration No. LA-0760-S-102-S describes and shows a 10 mm long Ir-192 seed encapsulated firmly inside a solid titanium/nickel wire. The Ir-192 seed is inserted into a hole drilled into an end of the titanium/nickel wire.

Registration No. LA-0760-S-105-S describes and shows a P-32 source. A thin film of P-32 is deposited within a carrier tube. The carrier tube is inserted into a cylindrical cavity at an end of a nickel/titanium tube, which has been welded on a nickel/titanium wire. A tungsten wire marker is inserted into the tube at the distal end of the carrier tube. A nickel titanium plug is inserted in the distal tip of the tube cavity and then welded to form a seal.

Handbook of Vascular Brachytherapy, ed. Ron Waksman and Patrick W. Serruys, Martin Dunitz Ltd, 1998, London at pages 489–497 show a brachytherapy source delivery system in which a "train" of several miniature cylindrical encapsulated sources containing Sr-90/Y-90 is delivered to the angioplasty site through a catheter by means of a fluid.

Registration No. NR-569-S-101-S describes and shows encapsulated radioactive gold seeds. Each cylindrical seed contains a rod of gold, which is encased in a platinum sheath.

Registration No. GA-1061-S-101-S describes and shows a tube like source. The source is constructed by centering a platinum-iridium marker on the outer surface of a medical grade titanium inner tube, followed by a layer of Pd-103 suspended homogeneously in a water insoluble organic polymer matrix. The source is encapsulated by sliding an outer tube over the inner tube and laser welding both ends.

Registration No. NR-187-S-103-S describes and shows a substrate with adsorbed onto it either iodine-125 or cesium-131 or palladium-103 in liquid form. Substrates for iodine may be rods or balls of carbon, polytyrosine or an anion exchange resin. Also described is a solid piece of samarium-145. The source material is encapsulated in a cylindrical double-walled titanium capsule and sealed by laser weld.

Registration No. IL-136-S-338-S describes and shows iodine-125 absorbed on a solid silver bar and encapsulated in a cylindrical titanium capsule.

Registration No. IL-136-S-337-S describes and shows iodine-125 absorbed on anion exchange resin spheres and encapsulated in a cylindrical titanium capsule.

Registration No. CA0510S126S describes and shows palladium-103 electroplated on a metallic substrate or absorbed on ion exchange resin beads. The active element is then placed inside a titanium capsule, which is then welded on its ends to complete containment.

Depending on the type of tissue that has to be irradiated a choice for a radioactive isotope is to be made that is to be used in the radioactive brachytherapy source. The above described and practically used sources make use of a multitude of isotopes.

Still more potential isotopes are described in U.S. Pat. No. 5,342,283. A considerable number of tables show for various desired beta- or gamma radiation outputs which isotopes of which elements produce such desired radiation. The patent is directed to coating pieces of a first material with one or more layers of second etc. materials.

U.S. Pat. No. 5,302,369 shows a method of manufacturing glass spheres containing a radioactive isotope. The glass spheres have diameters between 5 and 75 micron. First the glass spheres are manufactured such that they contain a precursor of the desired radioactive isotope. Thereafter the glass spheres are irradiated by neutron radiation to convert the precursor into the desired radioactive isotope. Other elements present in the glass spheres are selected from the group consisting of elements that do not become radioactive during neutron irradiation and elements that have a half life that is sufficiently short so that the other elements altogether do not emit a significant amount of beta- or gamma radiation at the time of administration of the radiation.

Radioactive brachytherapy source materials for incorporation in a radioactive brachytherapy source come in various shapes. Well known from the abovedescri bed sources are spheres, microspheres, rods, pellets, cylindrically shaped, short rods, beads. Further known are ellipsoid like and lens like shapes.

In endovascular brachytherapy, especially for coronary applications, an encapsulated radioactive brachytherapy source is desired that can navigate short curves without getting stuck or piercing a catheter or vessel wall. Such a source preferably is not larger in diameter than about 1 mm. Consequently, the specific activity, i.e. the activity per unit mass, of the radioactive brachyhtherapy source material should be sufficiently high to allow the construction of a thin source with a sufficiently high source strength to limit treatment times to preferably no more than several minutes. Furthermore at least for certain endovascular brachytherapy applications a beta source may be desirable, i.e. a source that predominantly radiates beta radiation. Beta radiation has a relatively short range in tissue, i.e. the beta particles do not penetrate deeper into tissue than several millimeters. Thus an encapsulated radioactive brachytherapy source of beta radiation allows localized irradiation of the vessel wall without exposing other body parts of the patient to radiation. Furthermore radiation exposure of medical personnel residing close to the patient is minimized, allowing the irradiation procedure to be performed adjacent to the angioplasty procedure within the ordinary cathlab environment without need for extensive shielding. A problem encountered in beta radiation source materials used in practice is that the mean energy of the beta radiation of many radionuclides is on the low side for brachytherapy applications. Another problem encountered in beta radiation sources is a short half life. In fact, it is known from nuclear physics that generally the half life of beta emitting radionuclides is relatively short when the beta energy is high. Too short a half life results in logistics problems as a consequence of the fact that an installed source has to be replaced with a new source after a short period already. It is desired to produce the radioactive source material both economically and reliably. Reliability of supply is important to assure that decayed sources can be replaced in time and requires that the source material can be produced by means of readily available production facilities, including e.g. nuclear radio isotope production reactors.

Consequently, a need has remained for a radioactive brachytherapy source material that emits beta radiation of sufficiently high energy and has a sufficiently long half life, that can be produced at a sufficiently high specific activity to allow short treatment times that can be produced both economically and reliably and that will allow the construction of a thin, encapsulated radioactive brachytherapy source in which that material has been applied to navigate short curves in coronary vessels and that may also have applications in other brachytherapy fields.

SUMMARY OF THE INVENTION

An object of the invention is to provide a method of manufacturing radioactive brachytherapy source material comprising indium-114m in radioactive equilibrium with indium-114 as main radioactive isotopes, said method comprising manufacturing predefinedly shaped pieces of a substantially inorganic and inactive material comprising indium oxide, the indium in said indium oxide having an abundance of indium-113 substantially equal to or greater than its natural abundance and subsequently subjecting the predefinedly shaped pieces of material to neutron irradiation until a predetermined specific activity of indium-114m of at least one MegaBequerel per gram indium has been reached.

With the expression main radioactive isotopes as used throughout the present description and claims is meant that a therapeutic dose distribution about a radioactive brachytherapy source, i.e. a therapeutically relevant dose distribution, is mainly determined by said main radioactive isotopes. The expression mainly determined as used throughout the present description and claims means that the contribution and claims means that the contribution to the therapeutic dose distribution of radiation emitted by radionuchides other than indium-114m and indium-114 is less than ten percent of the contribution to the therapeutic dose distribution of radiation emitted by indium-114m and indium-114.

A further object of the invention is to provide such a method in which the predefinedly shaped pieces comprise substantially only indium oxide.

A still further object of the invention is to provide a radioactive brachytherapy source material comprising predefinedly shaped pieces of material of a substantially inorganic material comprising indium oxide, the indium, present in said indium oxide, comprising indium-114m in radioactive equilibrium with indium-114 as main radioactive isotopes, said indium-114m being present with a specific activity of at least one MegaBequerel per gram indium.

A still further object of the invention is to provide a radioactive brachytherapy source material comprising predefinedly shaped pieces of substantially only indium oxide, the indium, present in said indium oxide, comprising indium-114m in radioactive equilibrium with indium-114m as main radioactive isotopes, said indium-114m being present with a specific activity of at least one MegaBequerel per gram indium.

A still further object of the invention is to provide an encapsulated radioactive brachytherapy source comprising a radioactive brachytherapy source material, said radioactive brachytherapy source material comprising indium-114m in radioactive equilibrium with indium-114 as main radioactive isotopes and being made by providing predefinedly shaped pieces of a substantially inorganic and inactive material comprising indium oxide, the indium in said indium oxide having an abuncance of indium-113 substantially equal to or greater than its natural abundance and subjecting the predefinedly shaped pieces of material to neutron irradiation until a predetermined specific activity of indium-114m of at least one MegaBequerel per gram indium has been reached.

DETAILED DESCRIPTION

Indium is an element consisting in its natural form of two isotopes, the stable isotope indium-113 and the ever so slightly radioactive isotope indium-115. The half life of indium-115 is $4.4*10^{14}$ years, which for all practical purposes means that it is a stable isotope. The abundance of indium-113 in indium's natural form, i.e. its natural abundance, is 4.3%, the remainder being indium-115. From handbooks such as the International Commission on Radiological Protection (ICRP); Radionuclide transformations, energy and intensity of emissions; ICRP Publication 38; Pergamon Press, Oxford, 1983, and Firestone, R. B.; Table of isotopes; eight edition; 1998 update with CD-ROM; John Wiley & Sons; 1998, and from the abovementioned U.S. Pat. No. 5,342,283 it may be seen that one of indium's isotopes, namely indium-114, emits a beta particle of desired energy for use in endovascular brachytherapy, namely with an average beta energy of 0.78 MeV and a maximum beta energy of 2.0 MeV. However, its half life of 72 seconds is much too short for practical purposes. As is known from the handbooks indium-114m is produced by neutron irradiation of indium-113. Indium-114m appears to decay mainly into indium-114 via an isomeric transition with a half life of 49.5 days. Referring to international patent application WO 97/25102, the contents of which are herein incorporated by reference, by irradiating indium-113 with neutrons a radioactive brachytherapy source material may be obtained that on the one hand has a half life of 49.5 days, the half life of indium-114m, and on the other hand decays with clinically relevant beta radiation, the beta radiation emitted by indium-114.

Indium, however, is an extremely soft metal with a very low melting point of 156° C. That makes indium as such, i.e. in its metallic form, unfit to be used as a radioactive brachytherapy source material. U.S. Pat. No. 5,342,283 suggests in such a case to encapsulate the metal. In the case of indium that solution is not preferable. Beta radiation, even of the highest energies that are available, has a relatively short range. Such encapsulation leads to extra shielding of the beta radiation. Both intensity and energy decrease due to such encapsulation. Furthermore extra encapsulation also leads to a decrease of effective volume in which radioactive isotopes may reside. Thus it will also be more difficult to produce sufficient radioactive isotopes to arrive at a desired activity. Consequently it must be avoided that encapsulation takes place with more encapsulation material than absolutely necessary.

According to the invention it has been discovered that using indium oxide provides a material with a high indium content, is much stronger and harder than elemental indium and has a high melting point of 1910° C. The nuclear properties of oxygen are such that irradiation of the material with neutrons to produce In-114m does not result in the production of unwanted contaminant isotopes. The atomic concentration of indium in indium oxide equals ca. $3.1*10^{22}$ $cm^{-3}$ which is not much lower than that of elemental indium, namely $3.8*10^{22}$ $cm^{-3}$. Thus the volume of indium oxide source material needed to achieve a given source activity at a given number of In-114m per mol indium is only slightly larger than the volume of metallic indium at that same number of In-114m per mol indium, allowing the construction of small, thin sources. Indium oxide has a density of about 7.2 grams per cubic centimeter, which is comparable to that of elemental indium, namely 7.3 grams per cubic centimeter. Thus the amount of self-absorption of beta radiation within a piece of radioactive brachytherapy source material of given dimoensions will not increase due to the use of $In_2O_3$ instead of indium. Furthermore oxygen has a low atomic number of 8, so it does not give rise to unwanted increase of the production of unwanted Bremsstrahlung or characteristic X-rays upon self-absorption of the beta radiation within the source material.

The indium oxide may be predefinedly shaped in various shapes and subsequently subjected to neutron irradiation. This approach minimizes the handling of radioactive materials resulting in a more economical and reliable production process. A number of techniques is available that may be used to shape the indium oxide into the desired shape. These include for example a number of ceramic forming techniques as described by for example Reed, James S.; Introduction to the Principles of Ceramic Processing; John Wiley & Sons; New York; 1988 and Terpstra, R. A.; Pex, P. P. A. C.; Vries, A. H. de; Ceramic Processing; Chapman & Hall; London; 1995, that may be used to produce so-called green bodies approximating the desired shape but not yet being fully consolidated and densified and are produced from powders. The green bodies are subsequently heat treated resulting in the consolidated and densified end product.

One such forming technique to produce green bodies described by Reed and by Terpstra et al is so-called dry pressing, which involves either uniaxial or isostatic pressing of the powder in a mold. In this way shapes like pellets, blocks, bars, rods, tubes, spheres, ellipsoid or lens-like shapes etc. may be fabricated.

Alternatively, the powder may be mixed with a suitable binder and possible other additions, in order to improve the compacting behavior of the powder in the mold.

Alternatively, a sufficiently cohesive and plastic mixture of powder, binder and possible other additives may be forced through a rigid die, resulting in elongated shapes of uniform cross-section, such as wires, bars, rods and tubes. This forming technique is called extrusion.

Alternatively, a mixture of the powder with a thermoplastic polymer resin or wax may be heated and injected into a cooled mold. This so-called injection molding technique allows the fabrication of simple but also relatively complex shapes. Current technology allows the injection molding of bodies with a volume less than about 1 $mm^3$, see for example Burg, T. v.d.; Metaal en Kunststof; vol. 23/24, pag. 26–27; 1998 (in Dutch).

The green bodies manufactured via techniques such as the ones described above are dried and possibly subjected to surface finishing if considered necessary, and are finally heat treated.

This heat treatment may include preheating to remove binders and other additives amongst which organic materials like the abovementioned thermoplastic polymer resin or wax and to eliminate gaseous products of decomposition and oxidation. This step must be carried out carefully to avoid damaging of the body due to stresses resulting from shrinkage, build up of gas pressure etc.

Following preheating the bodies are sintered at a temperature exceeding one half or two thirds of the melting point. The objective of sintering is to consolidate the product, by joining together the individual particles resulting in an end product, which has sufficient density and strength for the intended application.

Sintering may be done either under atmospheric pressure or under higher pressure. Higher pressures generally increase the sintering rate. Sintering may take place under regular atmospheric composition or under selected gas atmospheres. Indium oxide in the form of $In_2O_3$ may dissociatively decompose into $In_2O$ plus $O_2$, both gases at the sintering temperature. This decomposition reaction is occurring in the intermediate and final stages of sintering and leads to gas formation inside the spheres. This makes attainment of a low porosity product difficult if the reaction rate is too high. Similar problems are experienced during sintering of $SnO_2$ doped $In_2O_3$, generally referred to as ITO. If low porosity $In_2O_3$ is to be produced the decomposition reaction must be suppressed. This suppressing can be attained by using a sufficiently oxidizing atmosphere and keeping the sintering temperature low. Sintering with an elevated oxygen pressure will also be helpful. Improved sintering of indium oxide can be obtained if sintering aids such as titanium oxide (0.25–0.5 wt. %) or vanadium oxide (±1 wt. %) are used. These additives are mixed with the indium oxide starting material and reduce both sintering temperature and limit exaggerated grain growth, resulting in an end product of near theoretical density and high strength.

Information about the sintering of indium oxide and ITO and about useful sintering additives can be found in the following articles, which also provide examples of a number of differently shaped indium oxide bodies produced by means of dry uniaxial and isostatic pressing and wet uniaxial pressing: Wit, J. H. W. de; Laheij, M.; Elbers, P. F.; Grain growth and sintering of $In_2O_3$; Science of Ceramics, vol. 9, pag. 143–150; Nadaud, N.; Kim, D.-Y.; Boch, P.; Titania as a sintering additive in indium oxide ceramics; J. Am. Ceram. Soc., vol. 80, no. 5, pag. 1208–1212; Nadaud, N.; Boch, P.; Influence of $TiO_2$ additives on the microstructure of $In_2O_3$ ceramics; Ceramics International, vol. 22, pag. 207–209; Nadaud, N.; Boch, P.; Indium oxide ceramics with titania additions, Key Engineering Materials; vols. 132–136; pag. 928–931; Nadaud, N.; Nanot, M.; Boch, P.; Sintering and electrical properties of titania and zirconia containing $In_2O_3$—$SnO_2$ (ITO) ceramics; J. Am. Ceram. Soc., vol. 77, no. 3, pag. 843–846; Son, J-W; Kim, D-Y; Enhanced densification of $In_2O_3$ ceramics by presintering with low pressure (5 MPa); J. Am. Ceram. Soc., vol. 81, no. 9, pag. 2489–2492; Bates, J. L.; Griffin, C. W.; Marchant, D. D.; Garnier, J. E.; Electrical conductivity, Seebeck coefficient and structure of $In_2O_3$—$SnO_2$; Am. Ceram. Soc. Bull., vol. 65, no. 4, pag. 673–678; Chandra Babu, K. S.; Singh, D.; Srivastava, O. N.; Investigations on the mixed oxide material $TiO_2$—$In_2O_3$ in regard to photoelectrolytic hydrogen production; Semicond. Sci. Technol., vol. 5, pag. 364–368; Vojnovich, T.; Bratton, L. J.; Impurity effects on sintering and electrical resistivity of indium oxide; Ceram. Bull., vol. 54, no. 2, pag. 216–217; Suzuki, M.; Muraoka, M.; Sawada, Y.; Matsushita, J.; Sintering of indium tin oxide with vanadium oxide additive; Materials Science and Engineering, vol. B54, pag. 46–50.

As starting material for the above ceramic forming processes, commercially available indium oxide powder may be used. The powder may contain the natural element indium, with a In-113 abundance of 4.3%, or it may be isotopically enriched to contain an increased percentage of In-113. Commercially available enriched material is available with an In-113 abundance up to almost 100%. The advantage of using enriched material is a higher specific activity of In-114m upon neutron activation, thus saving activation costs and allowing the construction of smaller, thinner encapsulated radioactive brachytherapy sources.

There may be reasons for beneficiation of the starting powder properties, as discussed by Reed, for example via comminution by means of milling to decrease the size of the powder particles in order to improve the properties of the end product.

A way to produce fine indium oxide powder via a sol-gel approach is described by Bones, R. J. and Woodhead, J. L., in British Patent 1351113. This process allows the production of substantially spherical or irregularly shaped particles with a mean size between 1 and 200 $\mu$m. Shape and size can be controlled by means of a number of process parameters, although the size distribution around the mean is relatively broad. Specifically mentioned is the possibility to produce particles within a size range of 1 and 5 $\mu$m for sintering purposes. An alternative sol-gel method is described in Perez-Maqueda, L. A.; Wang, L.; Metijevic; Nanosize indium hydroxide by peptization of colloidal precipitates; Langmuir, vol.14, no. 16, pag. 4397–4401. Sintering additives as described hereinbefore can be added homogeneously with relative ease by addition as a nitrite or chloride salt during sol preparation.

Instead of using the sol-gel approach to produce a powder for subsequent forming and sintering, one may apply sol-gel chemistry to obtain the desired shape more directly. Examples are sol-gel coatings of metal oxides such as indium oxide or ITO onto substrates, the sol-gel production of fibers, monoliths, membranes, catalysts etc. as described in for example Pierre, A. C.; Introduction to sol-gel processing; Kluwer Academic Publishers, 1998 and Jones, R. W.; Fundamental principles of sol-gel technology, The Institute of Metals, London, 1989.

A particularly interesting source material comprises indium oxide microspheres. An encapsulated radioactive brachytherapy source may be constructed using one or more of such spheres. The use of multiple, substantially uniformly sized spheres, aligned in a row within a thin tubular capsule as described hereinbefore, allows the construction of a so called line source that is particularly suited to irradiate a segment of a coronary artery. Moreover, in order to facilitate advancement of such a line source via a catheter towards a lesion, the tubular capsule may be made from a flexible material such as a metal. In this case the use of indium oxide spheres, as opposed to e.g. a rod, assures that the flexibility of the source is not compromised by the presence of the source material. Furthermore the use of microspheres consisting primarily of indium oxide, in which the indium may be enriched in In-113, minimizes the volume necessary to achieve sufficient activity, thus allowing the construction of a thin source.

A multitude of references is available which describe how to produce metal oxide spheres, a category comprising indium oxide spheres. An overview is given in Wilcox, D. L. (1995); Berg, M.: Microsphere fabrication and applications: An overview; Mater. Res. Soc. Symp. Proc., vol. 372, pag. 3–13. Wilcox distinguishes four different methods, to which the methods described by Pickles (Pickles, C. A, (1983); Mclean, A.; Production of fused refractory Oxide Spheres and Ultrafine Oxide Particles in an Extended Arc; Ceramic Bulletin, vol. 62, no. 9, pag. 1004–1009), using a plasma arc, and by Dreizin (Dreizin, E. L., (1995); Uniform Solid and Hollow Metal Spheres: Formation in a pulsed Micro-Arc and Applications; Mater. Res. Soc. Symp. Proc., vol. 372, pag. 263–268), employing a micro plasma arc to produce spheres from a consumable anode, must be added.

Preferably for indium oxide spheres for use in an encapsulated radioactive brachytherapy source, solid spheres with a diameter of 100–1000 micrometer are desired, preferably with a high dimensional accuracy. Furthermore it is preferable that the loss of starting material during sphere production is low, especially if relatively costly enriched starting material is employed. Of the methods described by Wilcox, by Pickles and by Dreizin the most preferable one appears to be the method where spheres are made by feeding a liquid through a vibrating nozzle, resulting in the formation of droplets with a narrow size distribution. This process has several variables that can be used as steering parameters to optimize the production process. Therefore only a general outline is presented here.

In order to obtain spherical pieces of indium oxide by means of the vibrating nozzle process a number of steps has to be gone through. It starts with the production of a suitable precursor liquid.

A liquid precursor for indium oxide can for example be a suspension of indium oxide powder in a suitable solvent. Use of a suspension is described in U.S. Pat. No. 4,671,909 of Torobin. The suspension may for example consist of powder particles in water containing ammonium alginate, as described in U.S. Pat. No. 5,472,648 of Alisch et al. Alternatively, the liquid precursor may consist of an indium hydroxide sol, to which for example polyvinyl alcohol is added to adjust the viscosity of the liquid. Methods for the production of indium hydroxide sols have been mentioned hereinbefore.

The next step is feeding the liquid through a vibrating nozzle. As a result thereof sphere formation of liquid spheres takes place through interfacial forces.

The process of forming droplets with a narrow size distribution from the liquid is extensively described in various articles and patents including Schneider, J. M.; Hendricks, C. D.; Source of uniform sized liquid droplets; The Review of Scientific Instruments, vol. 35, no. 10, pag. 1349–1350; Lindblad, N. R.; Schneider, J. M.; Production of uniform sized liquid droplets, J. Sci. Instrum., vol. 42, pag. 635–638; Hendricks, C. D.; Babil, S.; Generation of uniform 0.5–10 μm, solid particles; J. Phys. E: Sc. Instrum., vol. 5, pag. 905–910; Calliger, R. J.; Turnbull, R. J.; Hendricks, C. D.; Hollow drop production by injection of gas bubbles into a liquid jet; Rev. Sc. Instrum. vol. 48, pag. 846–51; Foster, C. A.; Kim, K.; Turnbull, R. J.; Hendricks, C. D.; Apparatus for producing uniform solid spheres of hydrogen; Rev. Sc. Instrum., vol. 48, pag. 625–631; Hendricks, C. D.; Rosencwaig, A.; Woerner, R. L.; Koo, L. C.; Dressler, J. L.; Sheroman, J. W.; Weinland, S. L.; Jeffries, M.; Fabrication of glass sphere laser fusion targets; J. Nucl. Mat., vol. 85/86, pag. 107–111; Torobin, L. B.; Methods of making hollow porous microspheres; U.S. Pat. No. 4,671,909; Brandau, E.; Huschka, H.; Kadner, M.; Schröder, W.; Method for manufacturing spherical particles out of liquid phase; U.S. Pat. No. 5,183,493; Brandau, E.; Huschka, H.; Kadner, M.; Schröder, W.; Process and apparatus for preparing particles from a liquid phase; European patent no.0467221; Theisen, W.; Brauneis, E.; Pirstadt, B.; Process and device for producing microspheres; U.S. Pat. No. 5,500,162; Kim, K.; Fabrication of glass micro- and nanospheres from liquid precursors using droplet generation and sol-gel processing; Mater. Res. Soc. Symp. Proc. vol. 372, pag. 25–32.

After sphere formation the liquid spheres must be solidified to preserve their form. Solidification of a sol is done via gelation. The easiest method to cause gelation in a water based metal hydroxide sol is by increasing the pH value. Two processes are used in the art, called external gelation and internal gelation. External gelation comprises immersion of the sol droplets into a fluid that causes fast gelation of the sol. Examples of such fluids are ammonia gas and an aqueous solution of ammonia. In this method gelation is induced by the surrounding medium. Internal gelation is caused by the addition of a gelling agent to the sol, prior to droplet formation. In this case gelation is not starting directly, but there is a delay in time before the reaction takes off.

Solidification of alginate droplets can be achieved by immersion in an solution containing metal ions, such as an aqueous solution of $CaCl_2$, resulting in gelation of the alginate solution.

After gelation the spheres must be washed and then dried to remove the solute. Drying must be executed with some care. Too fast drying will cause formation of a semi-dry shell and subsequently the sphere will either blow up like a balloon or be fragmented. So a porous aerogel is formed of nanosized indium hydroxide particles. During the drying stage the sphere is expected to show shrinkage. The amount of shrinkage is amongst others dependent on the solids content of the indium hydroxide sol.

Drying is followed by calcination. Calcination is the process where the indium hydroxide is transformed into indium oxide particles, by heating them above the decomposition temperature (between 150° C. and 280° C.) of the hydroxide. Calcination must be executed with great caution. If it proceeds too fast internal steam pressure may build up leading to rupture or explosion of the spheres.

The resulting porous indium oxide spheres may be sintered to increase their density and strength. Sintering of indium oxide has been discussed hereinbefore. Sintering additives can be added homogeneously to the starting liquid by addition as a nitrite or chloride salt during sol preparation.

Though indium oxide may be available in pure form just like any other compound the higher the purity the higher the price. Moreover, it is advantageous to deliberately add certain sintering aids to the starting material in order to obtain a better end product, as has been argued hereinbefore. Besides indium oxide certain additional elements may be allowed in the indium oxide used in the composition of the radioactive brachytherapy source material.

A first requirement for such allowed additional elements is that after neutron irradiation the radiation of the radioisotopes produced from the additional elements (contaminant radioisotopes) does not significantly influence the therapeutic dose rate distribution. That means that if the spatial dose rate distribution of In-114m/In-114 for a certain purpose has been determined based upon a predefined shape of pure indium oxide (the therapeutic dose rate distribution) additional radiation originating from the contaminant radioisotopes does not contribute more to the total dose rate distribution than ten percent of the therapeutic dose rate distribution at any point within the therapeutically relevant region and that the dose rate to personnel due to additional radiation originating from the contaminant radioisotopes does not exceed one hundred percent of the dose rate due to radiation emitted by indium-114m and indium-114.

A second requirement is that the radiation of contaminant radioisotopes does not significantly raise the dose per treatment of the (hospital) personnel that resides at close distances from the patient. Here significantly means that the dose received by the personnel due to the contaminant radioisotopes is less than one percent of the dose received from the source containing only the In-114m/In-114 isotope.

A third requirement is that shielding requirements in apparatuses and devices in which sources according to the invention are being shipped, stored or used do not change.

These three requirement are met if either of two other requirement are met.

The first other requirement is that the additional elements are restricted to elements that have such a low neutron activation cross section in comparison to the cross section for the production of In-114m from In-113 that the amount of contaminant radioisotopes remains sufficiently low.

The second other requirement is that the half life of each of the contaminant radioisotopes produced from an additional element during neutron activation is much lower than the 49.5 day half life of In-114m, more specifically that the half life is less than about one day, so that so-called cooling of the radioactive brachytherapy source material for a limited number of days is sufficient for the contaminant radioisotopes to decay to insignificant levels.

When either of these two other requirements is met automatically the first three requirements are met.

However, there is a fourth requirement that also has to be met.

The fourth requirement is that the neutron capture cross section of an additional element is less than 200 barn. In that way it is achieved that the indium in the indium oxide is not shielded from the incoming neutrons by the atoms of the additional element.

It is noted that a very long half life results in a relatively low activity upon activation, compared to the activity of a radioisotope with a similar activation cross section but a short half life. Thus an additional element that meets the above four requirements may still give rise to one or more contaminant radioisotopes with a very long half life. Therefore a desirable property of the contaminant radioisotopes is that they have a half life that is not extremely long since this may give rise to a radioactive waste problem for the radioactive brachytherapy source material and the encapsulated radioactive brachytherapy source according to the invention. The group of additional elements that fit the abovementioned requirements is defined as the group consisting of elements that essentially do not become radioactive during neutron irradiation and elements that have a half life that is sufficiently short so that said selected elements do not emit a significant amount of beta- or gamma radiation at the time of application of the source material in a radioactive brachytherapy source.

The abovementioned requirements lead to the following allowed additional elements: hydrogen, lithium, beryllium, carbon, nitrogen, oxygen, fluorine, sodium, magnesium, aluminum, silicon, phosphorus, sulfur, potassium, calcium, titanium, vanadium, manganese, iron, nickel, copper, gallium, germanium, arsenic, strontium, zirconium, niobium, rhodium, tin, iodine, barium, platinum and lead. Preferably the additional elements are limited to hydrogen, beryllium, carbon, oxygen, fluorine, magnesium, aluminum, silicon, titanium, vanadium and manganese, since these combine a preferred low atomic number (Z<25) with a very low amount of contaminant radio isotopes at the time of the application.

An increase in specific activity of the radioactive brachytherapy source material, and as a consequence smaller encapsulated radioactive brachytherapy sources, can be achieved when instead of naturally available indium use is being made of indium enriched in In-113. Indium enriched with In-113 isotope is commercially available up to enrichment of close to 100% In-113.

What is claimed is:

1. Radioactive brachytherapy source material comprising indium-114m in radioactive equilibrium with indium-114 as main radioactive isotopes made by providing predefinedly shaped pieces of a substantially inorganic and inactive material comprising indium oxide, the indium in said indium oxide having an abundance of indium-113 substantially equal to or greater than its natural abundance and subjecting the predefinedly shaped pieces of material to neutron irradiation until a predeterminded specific activity of indium-114m of at least one MegaBequerel per gram indium has been reached.

2. Radioactive brachytherapy source material comprising predefinedly shaped pieces of material of a substantially inorganic material comprising indium oxide, the indium, present in said indium oxide, comprising indium-114m in radioactive equilibrium with indium-114 as main radioactive isotopes said indium-114m being present with a specific activity of at least one MegaBequerel per gram indium.

3. Radioactive brachytherapy source material comprising predefinedly shaped pieces of substantially only indium oxide, the indium, present in said indium oxide, comprising indium-114m in radioactive equililbrium with indium-114 as main radioactive isotopes, said indium-114m being present with a specific activity of at least one MegaBequerel per gram indium.

4. Radioactive brachytherapy source material according to any one of claims 1–3 in which the source material is encapsulated to form an encapsulated radioactive brachytherapy source.

5. Encapsulated radioactive brachytherapy source comprising a radioactive branchytherapy source material, said radioactive brachytherapy source material comprising indium-114m in radioactive equilibrium with indium-114 as main radioactive isotopes and being made by providing predefinedly shaped pieces of a substantially inorganic and inactive material comprising indium oxide, the indium in said indium oxide having an abundance of indium-113 substantially equal to or greater than its natural abundance and subjecting the predefinedly shaped pieces of material to neutron irradiation until a predetermined specific activity of indium-114m of at least one MegaBequerel per gram indium has been reached.

6. Encapsulated radioactive brachytherapy source comprising a radioactive branchytherapy source material, said radioactive brachytherapy source material comprising indium-114m in radioactive equilibrium with indium-114 as main radioactive isotopes and being made by providing predefinedly shaped pieces of a substantially inorganic and inactive material comprising indium oxide, the indium in said indium oxide having an abundance of indium-113 substantially equal to or greater than its natural abundance and subjecting the predefinedly shaped pieces of material to neutron irradiation until a predetermined specific activity of indium-114m of at least one MegaBequerel per gram indium has been reached.

7. Encapsulated radioactive brachytherapy source comprising as a radioactive brachytherapy source material substantially only a radioactive branchytherapy source material comprising indium-114m in radioactive equilibrium with indium-114 as main radioactive isotopes and being made by providing predefinedly shaped pieces of substantially only indium oxide, the indium in said indium oxide having an abundance of indium-113 substantially equal to or greater than its natural abundance and subjecting the predefinedly shaped pieces of material to neutron irradiation until a predetermined specific activity of indium-114m of at least one MegaBequerel per gram indium has been reached.

* * * * *